United States Patent
Ginner et al.

(10) Patent No.: US 11,086,133 B2
(45) Date of Patent: Aug. 10, 2021

(54) SOURCE MODULE AND OPTICAL SYSTEM FOR LINE-FIELD IMAGING

(71) Applicant: EXALOS AG, Schlieren (CH)

(72) Inventors: Laurin Ginner, Vienna (AT); Rainer Leitgeb, Vienna (AT); Marcus Dülk, Schlieren (CH)

(73) Assignee: EXALOS AG, Schlieren (CH)

( * ) Notice: Subject to any disclaimer, the term of this patent is extended or adjusted under 35 U.S.C. 154(b) by 0 days.

(21) Appl. No.: 16/709,534

(22) Filed: Dec. 10, 2019

(65) Prior Publication Data

US 2020/0201058 A1   Jun. 25, 2020

(51) Int. Cl.
| | |
|---|---|
| G02B 27/09 | (2006.01) |
| G01B 9/02 | (2006.01) |
| G02B 27/30 | (2006.01) |
| A61B 3/10 | (2006.01) |
| G01N 15/14 | (2006.01) |
| F21V 8/00 | (2006.01) |

(52) U.S. Cl.
CPC ..... *G02B 27/0966* (2013.01); *G01B 9/02091* (2013.01); *G01N 15/1436* (2013.01); *G02B 6/003* (2013.01); *G02B 27/0916* (2013.01); *G02B 27/0977* (2013.01); *G02B 27/30* (2013.01); *A61B 3/102* (2013.01)

(58) Field of Classification Search
CPC ..... G01B 9/02091; G02B 27/30; G02B 27/09
See application file for complete search history.

(56) References Cited

U.S. PATENT DOCUMENTS

| | | |
|---|---|---|
| 5,155,631 A | 10/1992 | Snyder et al. |
| 5,181,224 A | 1/1993 | Snyder |
| (Continued) | | |

FOREIGN PATENT DOCUMENTS

| | | |
|---|---|---|
| CN | 103115580 | 5/2013 |
| DE | 102006015387 | 10/2007 |
| (Continued) | | |

OTHER PUBLICATIONS

Ginner et al., Noniterative digital aberration correction for cellular resolution retinal optical coherence tomography in vivo, vol. 4, No. 8 / Aug. 2017 / Optica 924.

(Continued)

*Primary Examiner* — Kara E. Geisel
*Assistant Examiner* — Jarreas C Underwood
(74) *Attorney, Agent, or Firm* — Law Office of Michael Antone; Michael Antone

(57) ABSTRACT

A source module suitable for an optical coherence tomography system. The source module comprises a source operable to emit a divergent, source output beam either of circular cross-section (e.g. as output by a vertical cavity surface emitting laser) or of elliptical cross-section (e.g. as output by an edge-emitting semiconductor laser or diode). Collimation optics are provided to convert the source output beam into a non-divergent, collimated beam of elliptical cross-section having a major axis and a minor axis. A cylindrical lens is arranged with its plano axis aligned with the major axis of the elliptical collimated beam and its power axis aligned with the minor axis of the elliptical collimated beam so as to form a line focus extending along the major axis of the elliptical collimated beam.

8 Claims, 12 Drawing Sheets

(56) References Cited

U.S. PATENT DOCUMENTS

| | | | |
|---|---|---|---|
| 5,506,719 A | | 4/1996 | Murakami et al. |
| 5,566,016 A | * | 10/1996 | Lee .................... G02B 26/125 359/206.1 |
| 5,632,083 A | * | 5/1997 | Tada .................... B23K 26/032 29/827 |
| 6,396,616 B1 | | 5/2002 | Fitzer et al. |
| 7,400,457 B1 | * | 7/2008 | Gayer ................ G02B 27/0927 359/709 |
| 7,745,836 B2 | * | 6/2010 | Song .................. H01L 33/0045 257/82 |
| 8,049,133 B2 | * | 11/2011 | Oba .................... B23K 26/0604 219/121.65 |
| 10,799,111 B2 | * | 10/2020 | Schmoll ............. G01B 9/02032 |
| 2002/0131049 A1 | * | 9/2002 | Schmitt ................ G02B 6/2773 356/479 |
| 2006/0086941 A1 | * | 4/2006 | Han .................... H01L 33/0045 257/79 |
| 2007/0159639 A1 | | 7/2007 | Teramura et al. |
| 2010/0171931 A1 | * | 7/2010 | Kessler ................ H04N 9/3132 353/31 |
| 2010/0280315 A1 | * | 11/2010 | Pan ...................... A61B 5/0066 600/109 |
| 2014/0236002 A1 | * | 8/2014 | Wang .................. A61B 5/7275 600/427 |
| 2016/0223811 A1 | | 8/2016 | Plotkin et al. |
| 2019/0365220 A1 | * | 12/2019 | Frisken ..................... G06T 7/33 |

FOREIGN PATENT DOCUMENTS

| | | | |
|---|---|---|---|
| WO | WO 2018/136993 | * | 1/2017 |
| WO | 2018019374 | | 1/2018 |

OTHER PUBLICATIONS

Fechtig et al., Line-field parallel swept source interferometric imaging at up to 1 MHz, Sep. 15, 2014 / vol. 39, No. 18 / Optics Letters p. 5333.

Bonin et al Opt Letters 2010, In vivo Fourier-domain full-field OCT of the human retina with 1.5 million A-lines/s, Optics Letters / vol. 35, No. 20 / Oct. 15, 2010, p. 3432.

De Boer, Leitgeb et al Twenty-five years of optical coherence tomography: the paradigm shift in sensitivity and speed provided by Fourier domain OCT, vol. 8, No. 7 | Jul. 1, 2017 | Biomedical Optics Express p. 3248.

Cho et al, Quantitative assessment of touch-screen panel by non-destructive inspection with three-dimensional real-time display optical coherence tomography, Optics and Lasers in Engineering 68(2015) p. 50-57.

* cited by examiner (circular - background)

(short-x - comparative)

(long-x)

SOURCE MODULE AND OPTICAL SYSTEM FOR LINE-FIELD IMAGING

CROSS-REFERENCE TO RELATED APPLICATIONS

This non-provisional patent application claims the benefit of and priority to U.K. Patent Application No. 1820792.8, filed Dec. 20, 2018, which is incorporated herein by reference in its entirety.

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISC APPENDIX

Not Applicable

FIELD OF THE INVENTION

The invention relates to line-field illumination systems that use light from semiconductor light sources, such as light emitting diodes, semiconductor lasers, swept source semiconductor lasers and superluminescent diodes.

BACKGROUND OF THE INVENTION

Acquisition speeds have been advancing rapidly in modern imaging techniques. For example, in optical coherence tomography (OCT) acquisition speed has increased by several orders of magnitude during the last decade. Today, recently-developed laser sources allow even MHz "A-scan" rates to be achieved, where an A-scan refers to a single scan of intensity vs depth (see de Boer et al [1]). Such high-speed point scanning systems are already operating at the detection limit set by shot noise and by laser safety regulations. A potential way forward is parallel OCT, which in principle offers higher sensitivity due to the fact that the illumination can be treated as an extended source. Bonin et al [2] presented a parallel full-field swept source OCT system operating at 1.5 MHz equivalent A-scan rate. Bonin et al claim a minimal parallel acquisition speed of 100 Hz is needed to avoid substantial loss in sensitivity and structural compliance. This can however only be achieved in full-field OCT by using expensive high-speed sensor technology. In addition, full-field OCT lacks the confocal gating, that helps to suppress out-of-focus light that otherwise reduces the dynamic range of the sensor and ultimately the detection sensitivity. A potential alternative is line-field OCT, which retains partial confocal gating, as well as the sensitivity advantage of parallel acquisition (see Fechtig et al [3]). Those advantages hold also for any other line-field scanning imaging systems, such as line scanning laser microscopy or ophthalmoscopy. In general, line-field illumination allows for higher illuminance, when laser safety considerations set limits on the sample exposure.

The coupling of light emitted from an edge-emitting semiconductor light source into an illumination system is most commonly implemented by transforming the divergent elliptical cross-section beam emitted from the source into a circular cross-section beam and collimating it using collimation optics. This can be achieved by arranging two cylindrical lenses of different focal lengths orthogonal to each other separated from the output face of the (point) source by their respective focal lengths. Another approach to convert the divergent, elliptical cross-section beam into a circular, collimated one is to couple the source output beam into a single-mode fiber, the output of which is a circular, Gaussian beam. A spherical lens can then be arranged downstream of the fiber's output end to produce a collimated, circular beam. Fiber coupling is however accompanied by significant optical power losses. To compensate for any power losses, the source needs to output a higher power and thus be driven with a higher drive current. An increase in drive current is, however, associated with a decreased lifetime for the source.

For applications where a line focus is desired by the downstream optical system, this is generated after the collimation optics by placing a cylindrical lens in the circular, collimated beam. The cylindrical lens produces a line focus in one propagation plane, whereas in the orthogonal propagation plane the beam is not affected by the cylindrical lens. This situation is called anamorphic, since the cylindrical lens has resulted in unequal magnifications being applied along the two perpendicular axes orthogonal to the optical axis. This leaves no design freedom in where to place the lenses. For example, in line-field OCT, it is advantageous to be able to freely adjust the reference arm length, which is only possible if the beam is collimated. To achieve this another cylindrical lens is therefore needed to remove the anamorphism, this additional cylindrical lens being arranged after the line focus.

SUMMARY OF THE INVENTION

The light distribution after emission from an edge-emitting laser chip intrinsically has a non-circular, extended cross-section in far field that may be approximated as an ellipse. This property is exploited by certain embodiments of the invention to provide a line focus with more desirable properties compared with the standard approach of focusing a circular, Gaussian beam with a cylindrical lens.

According to a first aspect of the invention there is provided a semiconductor source module, comprising a source operable to emit a divergent, output beam of circular or elliptical cross-section. Collimation optics are arranged to convert the source output beam into a non-divergent, collimated beam of elliptical cross-section having a major axis and a minor axis. A line-focusing cylindrical lens having a plano axis and a power axis is also provided and is arranged with its plano axis aligned with the major axis of the collimated beam and its power axis aligned with the minor axis of the collimated beam so as to form a line focus extending along the major axis of the collimated beam.

In some designs, the collimation optics comprises a first collimating cylindrical lens which collimates the beam in a first plane and a second collimating cylindrical lens which collimates the beam in a second plane orthogonal to the first plane, the first and second collimating cylindrical lenses being spaced apart by a distance which defines the ratio between the respective diameters of the major and minor axes of the collimated beam, i.e. the aspect ratio. Designs of this kind allow a flexible collimation of divergent output beams of circular or elliptical shape into a collimated, elliptical beam with any desired aspect ratio. In other designs, the collimation optics comprises a spherical lens or an aspherical lens.

If the source generates an output beam of elliptical cross-section, then example sources are edge-emitting semiconductor sources, such as semiconductor lasers (sweepable or fixed wavelength), superluminescent diodes and light-emitting diodes. On the other hand, if the source generates an output beam is of circular cross-section, example sources include a vertical cavity surface emitting laser and an optical fiber (e.g. optical fiber laser, amplified spontaneous emission source, or optical fiber waveguide provided to deliver output from a separate source whose output is coupled into a distal end of the optical fiber).

Embodiments of the invention are capable of providing improved line-field illumination schemes by exploiting the intrinsic anamorphic beam properties of edge-emitting semiconductor sources such as light emitting diodes including organic light emitting diodes, superluminescent diodes, lasers and so forth. Although an elliptical profile causes loss of light when coupled into a single mode fiber, from its geometry it is intrinsically better suited to line illumination schemes. In contrast, when a Gaussian beam of circular shape is focused into a line using a collimating lens followed by a cylindrical lens, the resultant line focus suffers from a greater fall off of power along the line of the focus away from its peak value that lies on the optical axis and also greater fall off of power across the focus away from its peak value that lies on the optical axis, i.e. power fall off orthogonal to the line of focus compared to a line focus created with the optical configurations proposed herein.

For applications where asymmetric illumination is desired, the intrinsically elliptical profile output from an edge-emitting semiconductor source is used without first converting it via conventional collimating optics into a circular, collimated beam and in particular without first passing the output light through a single-mode fiber. By avoiding conventional collimation optics or fiber coupling, the full output power of the source is retained.

According to a second aspect of the invention there is provided an optical coherence tomography system, comprising: a semiconductor source module according to the first aspect of the invention, a beam splitter arranged to receive light output from the source module and to direct one component into a first, sample arm to an optical test sample and another component to a second, reference arm, and to recombine light received back from the first and second arms and direct the recombined light to a detector.

According to one implementation, the line focus of the divergent elliptical beam output from the source is performed with a combination of two cylindrical lenses for collimating the beam into a cross-sectional height and width matched to a third cylindrical lens which is used to focus the collimated beam into a line. This embodiment can also be used to generate a line focus from a divergent circular beam, such as output by an optical fiber or vertical cavity surface emitting laser. The output from the optical fiber may be generated in the fiber itself, e.g. the fiber may comprise an optical fiber laser or an amplified spontaneous emission (ASE) source, or the fiber may be a delivery conduit for the output from an external source, such as a laser or diode, the output of which is coupled into a distal end of the fiber.

Further example system applications of the source module are as follows: In a flow cytometer system in which a flow cell comprising a sample capillary tube is arranged so that the line focus intersects with sample in the capillary tube. In a display device comprising a display panel; and an edge-lit backlight unit with a light guide layer arranged under the display panel, the source module being arranged with its line focus aligned along an edge of the light guide layer, thereby to provide the backlighting. In a mirror deflection device comprising: a planar mirror, in which the source module is arranged to illuminate the planar mirror with a light beam of elliptical cross-section, said light beam being deflected by the mirror so as to change the aspect ratio of its cross-section, the source module being configured to output a beam of a cross-section specified to provide a desired cross-section in the light beam deflected from the mirror.

BRIEF DESCRIPTION OF THE DRAWINGS

This invention will now be further described, by way of example only, with reference to the accompanying drawings.

DETAILED DESCRIPTION

When describing an ellipse or elliptical shape we use the parameters 'a' and 'b' for the diameters of the major and minor axes of the ellipse. Their ratio a/b is referred to as the aspect ratio of the ellipse. While a circle can be defined as an ellipse with a unitary aspect ratio, i.e. a/b=1, for the purposes of this document, we do not consider a circle to be an ellipse, i.e. by 'ellipse' or 'elliptical' we mean an ellipse with a non-unitary aspect ratio.

Figure 1:
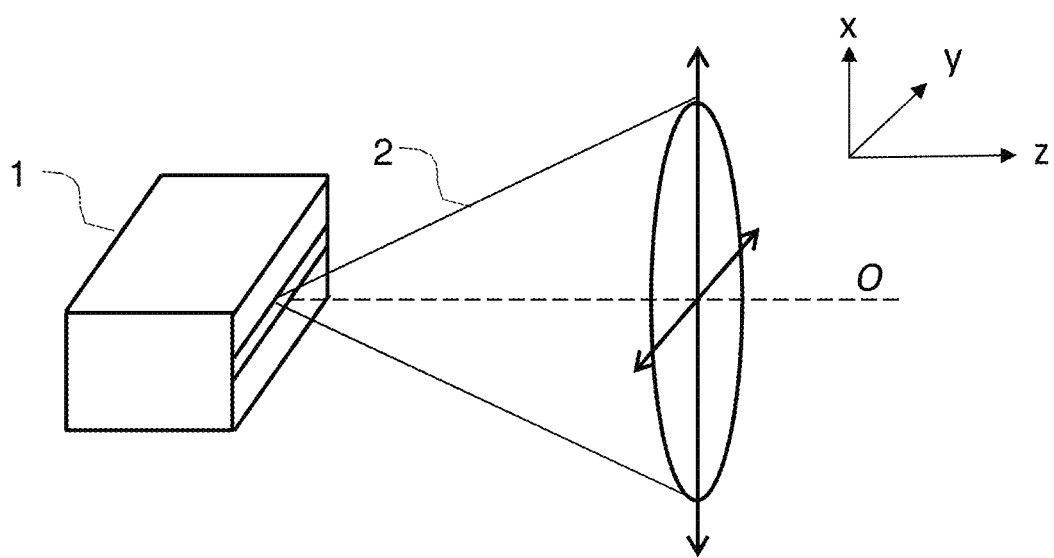
FIG. 1 is a schematic drawing of a generic edge-emitting semiconductor source with an elliptical cross-section output beam.

FIG. 1 is a schematic drawing of a generic semiconductor source 1 and the divergent elliptical beam shape 2 of its output. The semiconductor chip of the source is made of epitaxial layers extending in the yz-planes as schematically depicted. The illustrated output face of the chip is in the xy-plane. The source's output beam 2 is of elliptical shape in the far field, with the major (i.e. long) axis of the ellipse being in the x-direction, the minor (i.e. short) axis in the y-direction, and the optical axis O of the output beam in the z-direction. As is well known, the output beam characteristics of a semiconductor source are due to diffraction at the output face of the chip and the degree of ellipticity, divergence and other parameters of the output beam can be controlled somewhat through the cavity design.

Figure 2:
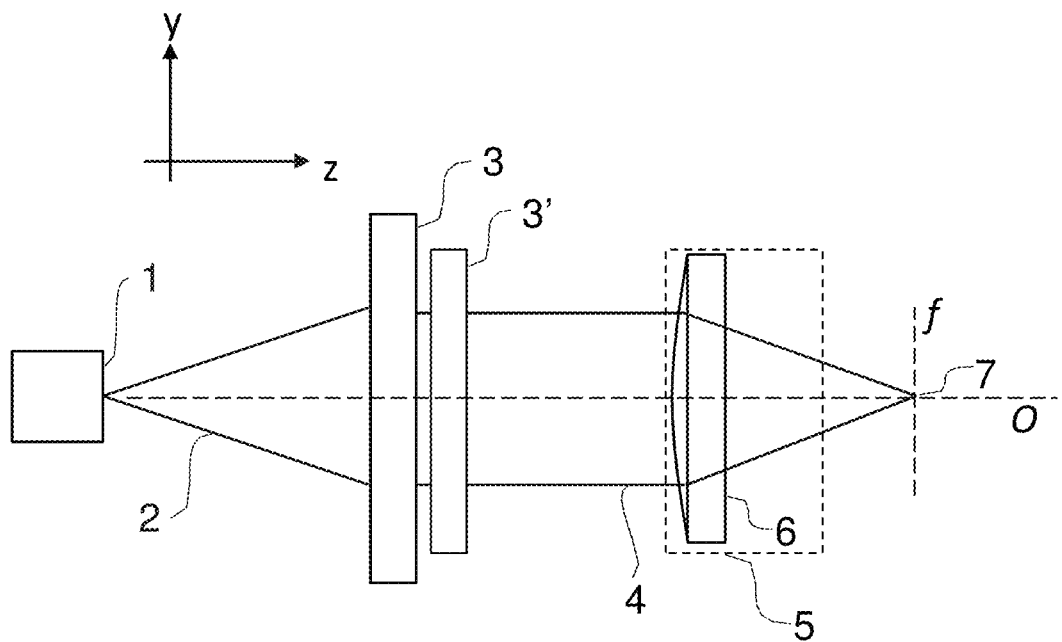
FIG. 2 is a plan view of a source module according to one embodiment including a cylindrical lens.

FIG. 2 shows a source module according to one embodiment with reference to an optical axis O in the z-direction. The divergent output beam 2 from the source 1 is collimated by collimation optics 3 into a collimated beam 4. The collimation optics 3 can for example be a spherical lens, aspherical lens or equivalent lens combination. After the collimation optics 3, the system may optionally include one or more further optical components 3' to homogenize illuminance across the beam cross-section. For example, a beam-shaping device may be provided for producing a close-to-rectangular shaped beam profile, a Powell lens, diffractive optics or phase plates. The collimated beam 4 can then be used for any desired line-field imaging modality, for line-field projection devices, or for coupling into one or more waveguides, such as waveguide arrays or optical fiber bundles. The downstream optical components are generically shown as optical sub-system 5. The optical sub-system 5 includes at its input a single cylindrical lens 6, or functionally equivalent lens or mirror combination, that focuses the elliptical collimated beam 4 to a line 7 in the focal plane f with the line focus extending in the x-direction (out of the plane of FIG. 2) and having a narrow width in the y-direction.

Figure 3:
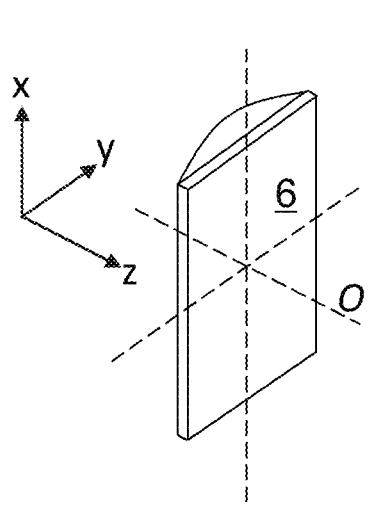
FIG. 3 is a perspective view of the cylindrical lens of FIG. 2.

FIG. 3 is a schematic perspective view of the cylindrical lens 6 of FIG. 2, where x is the plano axis, y is the power axis, and z (or O) is the optical axis.

Figure 4:
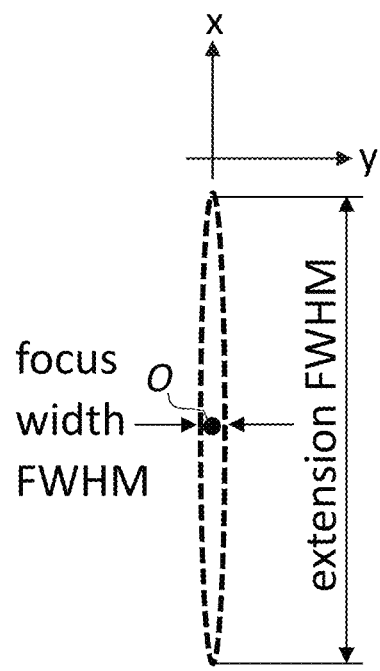
FIG. 4 is a view along the optical axis O of the line focus of the cylindrical lens of FIG. 2 in the focal plane of the cylindrical lens.

FIG. 4 is a view along the optical axis O of the line focus of the cylindrical lens of FIG. 2, with the focal plane of the cylindrical lens 6, which is a plane in xy, being the plane of the paper. The line focus has a focal extension in the x-direction and a focal width in the y-direction. The focal extension and width can each be measured in terms of the FWHM, 1/e2 or some other parameter that is suitable for measuring a falling profile, such as a Gaussian, compared with the peak, i.e. maximum, intensity at the optical axis. The dashed line in FIG. 4 represents the FWHM value for the intensity.

Figure 5A:
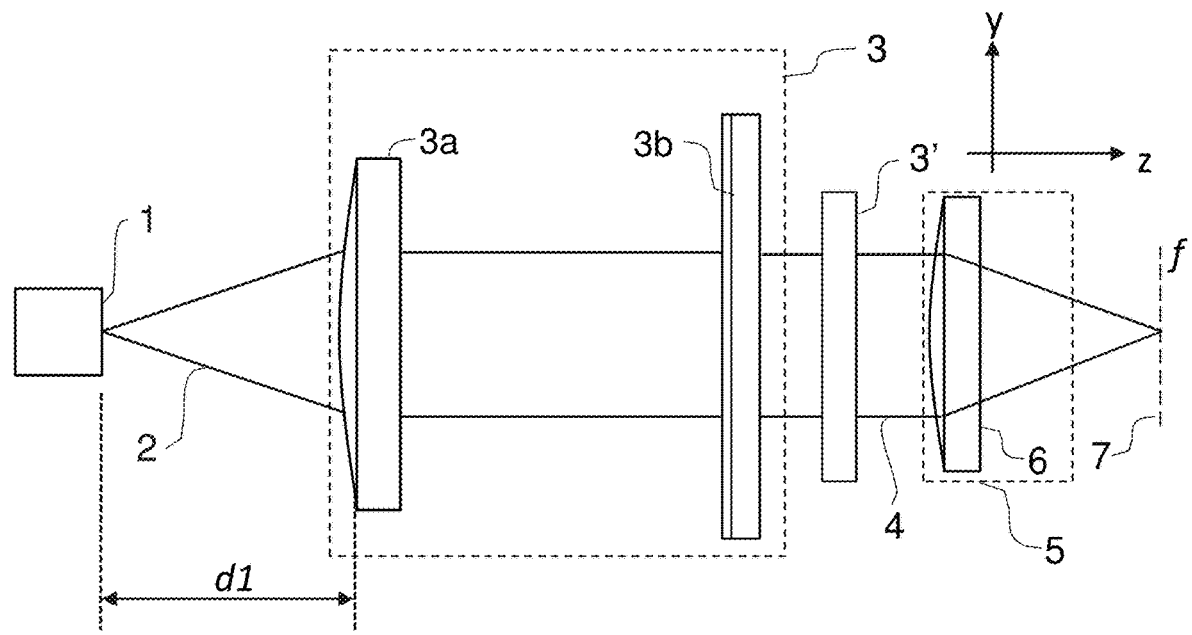
FIGS. 5A & 5B are respectively plan and side views of a source module according to another embodiment.
Figure 5B:
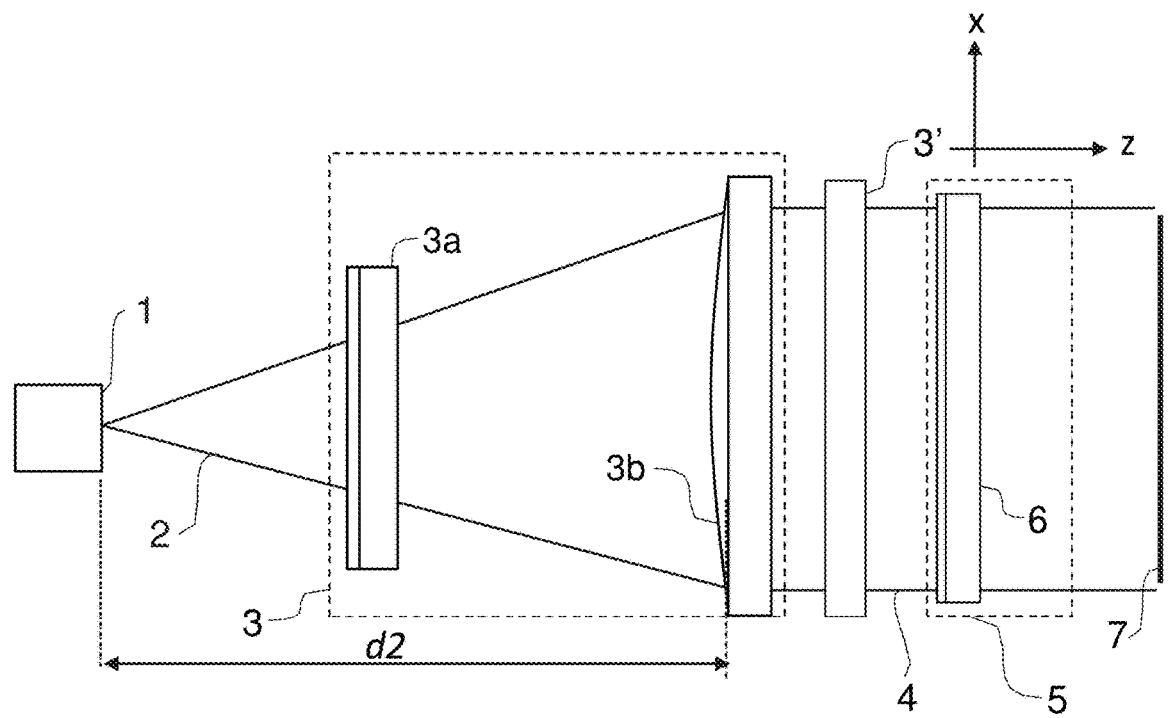

FIGS. 5A & 5B are respectively plan and side views of a source module according to another embodiment. The divergent output light 2 from the source 1 is collimated by collimation optics 3 comprising a first cylindrical lens 3a arranged a distance d1 from the source which collimates the beam in the yz-plane as shown in FIG. 3A, and a second cylindrical lens 3b arranged a distance d2 from the source (where d2>d1) which collimates the beam in the xz-plane as shown in FIG. 3B after letting the beam propagate further and hence diverge more. In other words, the first cylindrical lens 3a has its power axis in the y-direction and its plano axis in the x-direction, and the second cylindrical lens 3b has its power axis in the x-direction and its plano axis in the y-direction. By choosing the distances d1 and d2 between the source 1 and the first and second cylindrical lenses 3a, 3b and the focal lengths of the cylindrical lenses 3a, 3b, the collimated beam extension in the x- and y-directions can be controlled, thereby providing control of the ellipticity of the collimated beam output by the cylindrical lens combination 3a, 3b. In other words, the area of the collimated beam can be matched to the area of the cylindrical focusing lens 6 in the xy-plane, since the extension of the collimated beam is independently controllable in x and y.

An important additional point in relation to the arrangement of FIGS. 5A & 5B is that such an arrangement is not only suitable for transforming an elliptical cross-section, divergent beam from a source, such as an edge-emitting semiconductor source, into an elliptical cross-section, collimated beam, but is also suitable for transforming a circular cross-section, divergent beam from a source, such as an optical fiber or a vertical cavity surface emitting laser (VCSEL), into an elliptical cross-section, collimated beam. The embodiment of FIGS. 5A and 5B is thus suitable for generating a line focus from both a circular cross-section divergent beam and an elliptical cross-section divergent beam.

It will be understood that the order of the first and second cylindrical lenses 3a and 3b is arbitrary, the relevant factor being that their plano axes are orthogonal to each other. Further optical components 3' may be provided to homogenize illuminance across the beam cross-section as described above in relation to FIG. 2. An optical system 5 arranged downstream to receive the collimated output of the collimation optics 3 may for example include at its input a single cylindrical lens 6, or functionally equivalent lens or mirror combination, that focuses the elliptical collimated beam 4 to a line 7 in the focal plane f with the focus extension being in the x-direction and the focus width being in the y-direction.

We now compare performance of the proposed optical arrangements of FIG. 2 and FIGS. 5A & 5B for line focusing a collimated beam of three different shapes: namely a circular shape (representing a generic background example), an elliptical shape with the ellipse focused along its long side (i.e. major axis) in the following referred to as "short-x" due to the non-focused side being the shorter side (representing a comparative example), and an elliptical shape with the ellipse focused along its short side (i.e. minor axis) in the following referred to as "long-x" due to the non-focused side being the long side (representing an embodiment of the invention).

Figure 6:
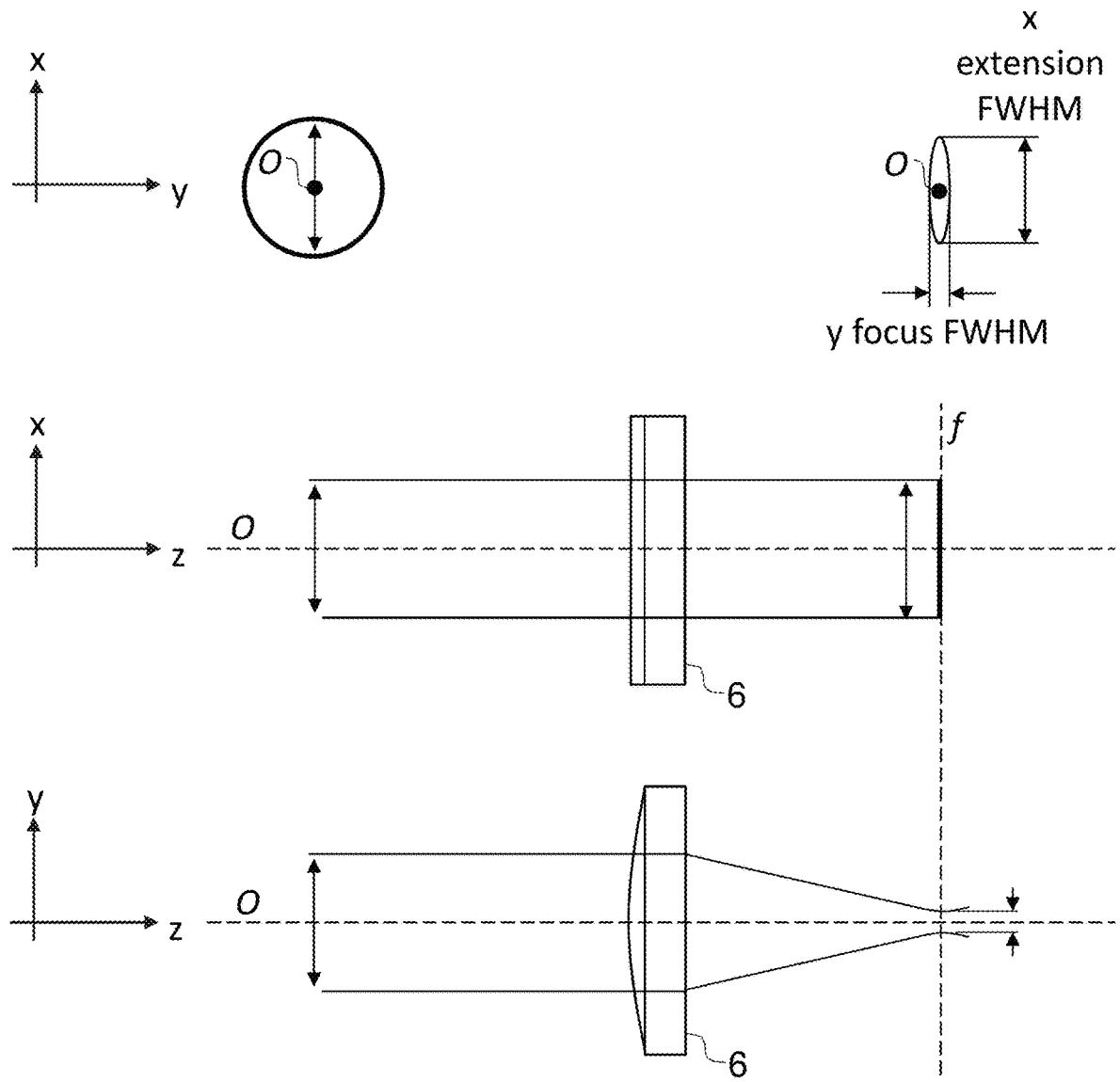
FIG. 6 shows a background example with a circular collimated beam incident on the cylindrical lens.

FIG. 6 shows various schematic views of the background example with a circular collimated beam incident on the cylindrical lens.

Figure 7:
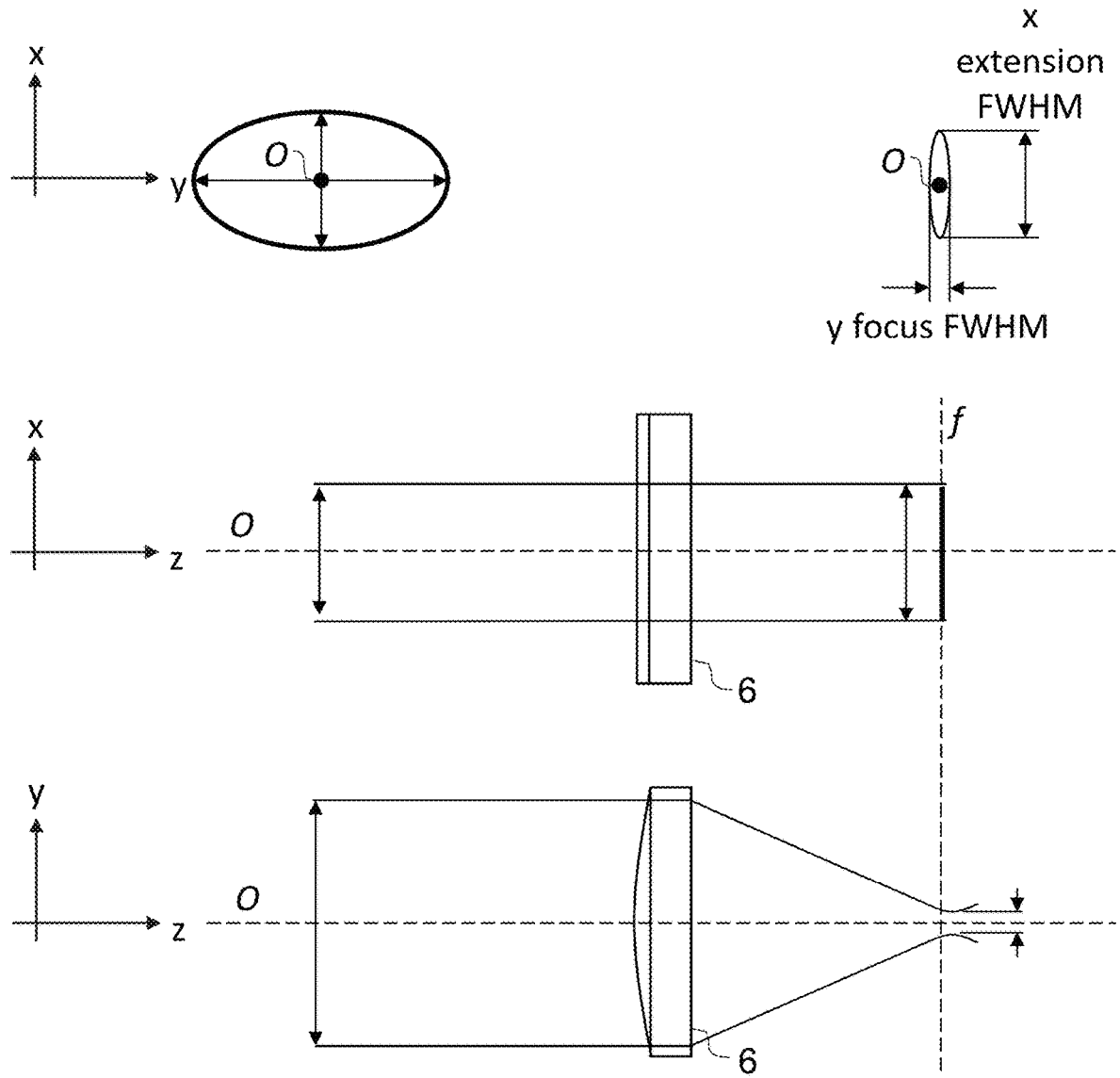
FIG. 7 shows a comparative example, labelled "short", with an elliptical collimated beam incident on the cylindrical lens with the ellipse having its minor axis in the x-direction and its major axis in the y-direction.

FIG. 7 shows various schematic views of the comparative example, labelled "short-x", with an elliptical collimated beam incident on the cylindrical lens with the ellipse having its minor axis in the x-direction and its major axis in the y-direction.

Figure 8:
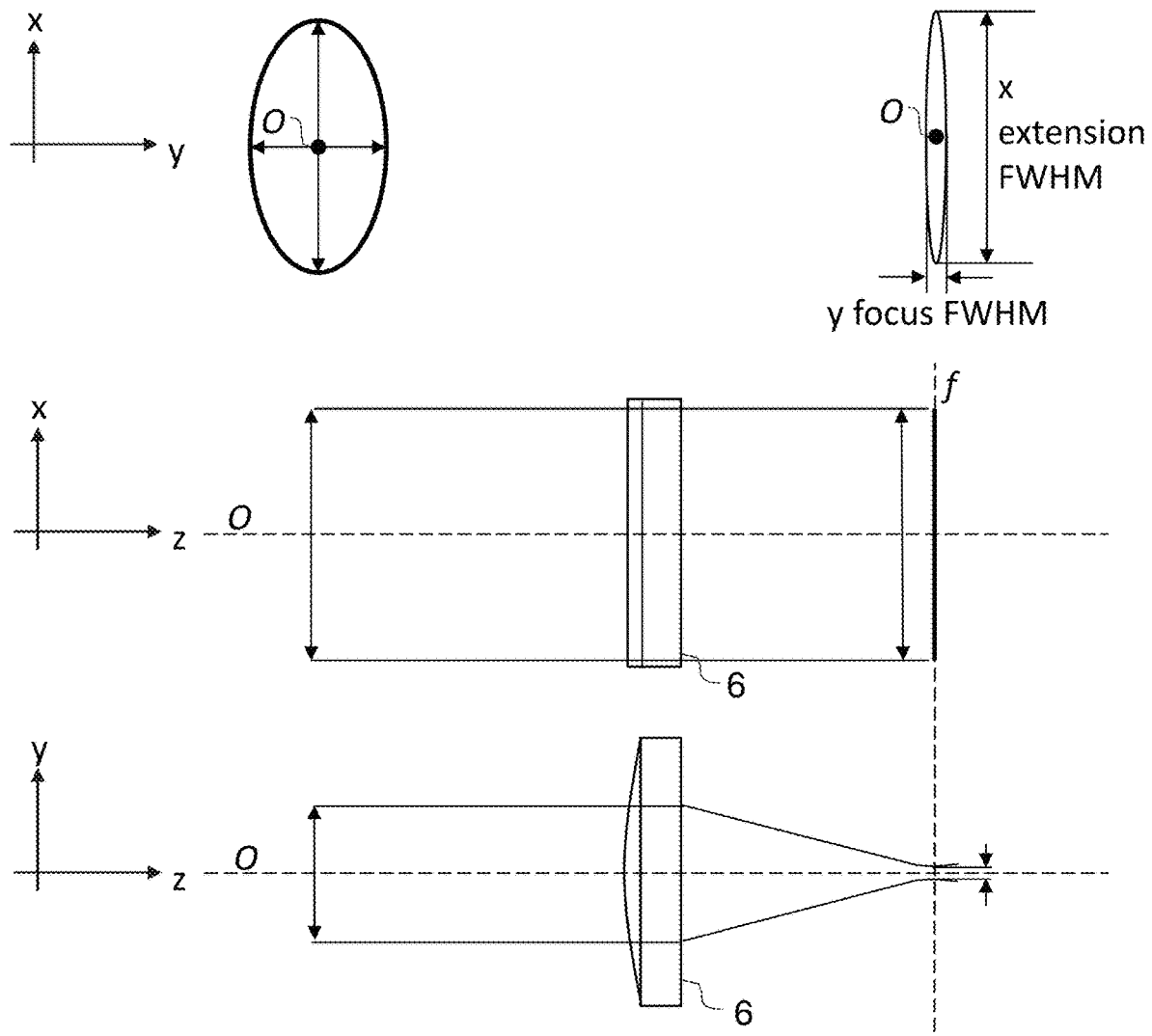
FIG. 8 shows an example according to an embodiment of the invention, labelled "long", with an elliptical collimated beam incident on the cylindrical lens with the ellipse having its minor axis in the y-direction and its major axis in the x-direction.

FIG. 8 shows various schematic views of an example according to an embodiment of the invention, labelled "long-x", with an elliptical collimated beam incident on the cylindrical lens with the ellipse having its minor axis in the y-direction and its major axis in the x-direction.

Each of FIGS. 6, 7 and 8 have the same lay out with representations in the xy-plane (top), yz-plane (middle) and xz-plane (bottom). The middle and bottom representations show plan and side views respectively of the collimated beam being focused in the focal plane f by the cylindrical lens 6. The top-left representation shows the collimated beam cross-section. The top-right representation shows the line focus in the focal plane f.

To test the two elliptical examples, we used a system as shown in FIG. 2 which employs a single achromat as component 3 followed by a cylindrical lens 6 to bring the light into a line focus. To test the circular example we used a collimated, circular Gaussian single-mode beam whose diameter was set equal to the major axis dimension of the elliptical beams. The light sources used were superluminescent diodes (SLDs), specifically Superlum (trade mark of Superlum Diodes Limited, Cork, Ireland) broadband light sources with model numbers SLD-CS-371-HP3-SM-840-I for the circular beam and SLD-340-UHP-T09-PD with a Thorlabs SLD driver for the elliptical beam (Thorlabs is a trademark of Thorlabs, Inc). These SLDs have a strong divergence of >15° which is collimated using a C110TMD-B lens from Thorlabs. The output beam of the SLD is an elliptical collimated beam with a long axis extension of 3770 µm and a short axis extension of 2030 µm. The collimation was controlled visually over a distance of 4 m.

FIG. 6 (circular; background): A circular cross-section, Gaussian beam is input into a cylindrical lens 6 aligned with its plano axis in the x-direction and its power axis in the y-direction to generate a line focus extending in the x-direction.

FIG. 7 (short-x; comparative): The plano axis of the cylindrical lens 6 is aligned with the short axis of the collimated elliptical beam in the x-direction and the power axis of the cylindrical lens is aligned with the long axis of the collimated elliptical beam in the y-direction to generate a line focus with a relatively short extension along the x-direction, the extension having a length approximately equal to the minor axis dimension of the ellipse.

FIG. 8 (long-x; embodiment): The plano axis of the cylindrical lens 6 is aligned with the long axis of the collimated elliptical beam in the x-direction and the power axis of the cylindrical lens is aligned with the short axis of the collimated elliptical beam in the y-direction to generate a line focus with a relatively long extension along the x-direction, the extension having a length approximately equal to the major axis dimension of the ellipse.

Figure 9:
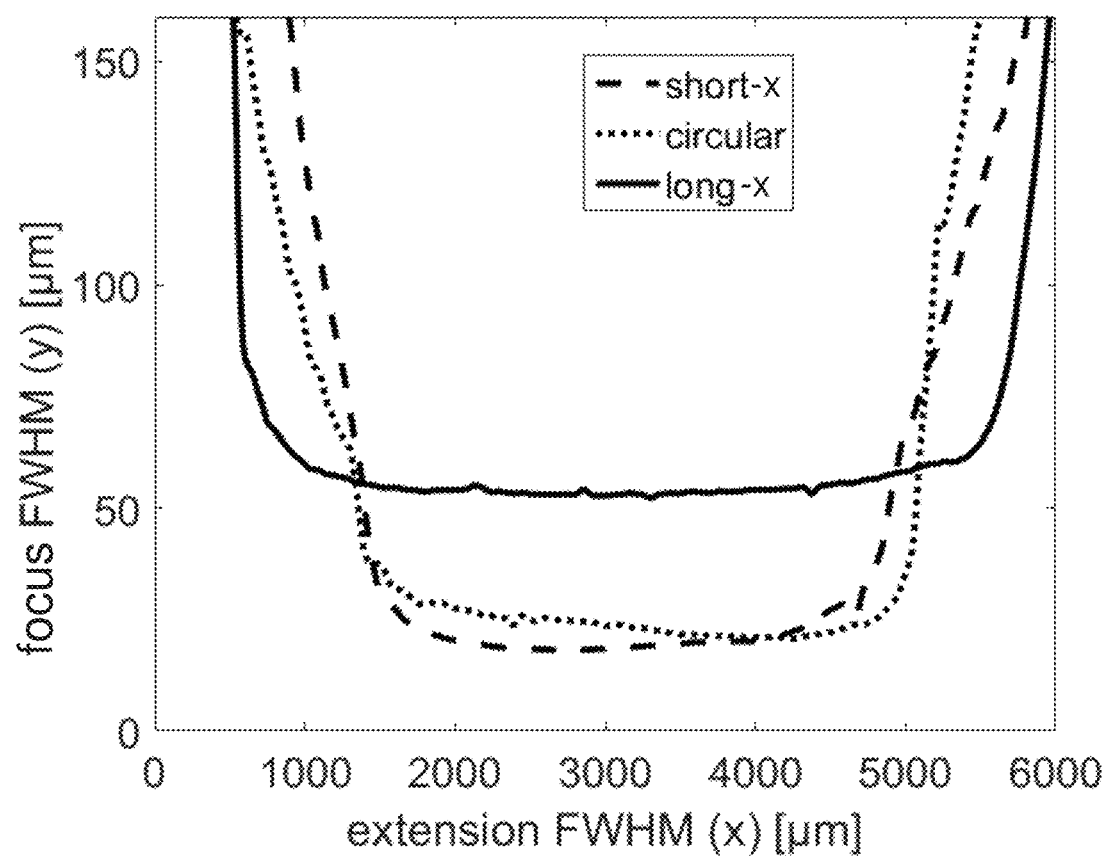
FIG. 9 is a graphical representation of test results from the examples of FIGS. 6, 7 and 8 plotting the extension of the line focus against the width of the line focus.

FIG. 9 is a graphical representation of test results from the examples of FIGS. 6, 7 and 8 plotting the extension of the line focus against the width of the line focus. We measured the variation in the width of the focus in the y-direction, through its full width half maximum (FWHM), as one moves away from the optical axis in the x-direction. As expected, the focus becomes increasingly more diffuse, i.e. less tight, the further one moves away from the optical axis in the x-direction. As a measure of the extension of the line focus along its length we measured the x-values either side of the optical axis at which the FWHM was 25% higher than the FWHM at the optical axis, i.e. the minimum FWHM. As can be seen from the graph, both the absolute values of the FWHM of the focus and their decrease along the x-direction is similar for the "circular" and "short-x" examples. In the "circular" example, the circular beam has a minimum FWHM of 20.7 µm. In the "short-x" example in which the longer side of the elliptical beam is focused, the minimum FWHM is 18 µm. From theory, we would have expected the "short-x" example to have a FWHM lower than that of the "circular" example by a factor of 1.8. The fact that our experimental results do not show this may be explained by imperfect collimation of the elliptical beam and/or by the presence of multiple modes in the source output. We note that higher order modes could be filtered out if desired, e.g. with a single mode fiber, but we did not do this. On the other hand in the "long-x" example, which focuses the shorter side of the elliptical beam, the line focus is less tight than the other two examples, having a minimum FWHM of approximately 60 µm, and the extension of the line focus is longer by approximately 1.5 mm as measured by the point at which a 25% increase in FWHM from the minimum occurs.

These results show that excellent results are achieved, superior to those for circular, collimated beams, when an elliptical, collimated beam is focused to a line focus along its longer dimension (i.e. long-x example). Specifically, for the same power in the collimated beam, we achieve a line focus which is 1.6 times longer. With a circular, collimated beam, increasing the beam diameter by 50% (i.e. increasing beam area and hence power by 2.25 times) increases the line focus length to about 90% of that achieved with the elliptical, collimated beam focused in its shorter dimension. In other words, using the "long-x" configuration of an elliptical, collimated beam allows less than half the power to be used in the beam that is input into the cylindrical lens used to create the line focus compared with a circular cross-section, collimated beam with the same x-extension. Moreover, in practice the power saving would be even better for an edge-emitting semiconductor source, since our proposed approach eliminates the power losses in conventional collimating optics that are conventionally used to convert an edge-emitting semiconductor source's divergent, elliptical output beam into a circular, collimated beam.

The proposed approach can therefore make more efficient use of the output power of a semiconductor source, so the source can be run at reduced output power, resulting in a longer source lifetime by taking advantage of the intrinsic ellipticity of a source's divergent output beam for devices that require a line focus to be inputted.

The above-described lens components, e.g. elements 3 (or 3a & 3b), 4 & 6, and the beam shaping optics 3', can be either refractive or diffractive elements, or combinations of both.

Moreover, the term 'lens' in this document is to be construed as encompassing functionally equivalent mirrors.

The examples use FWHM as the measure of the drop off in power away from the optical axis (z-axis) along the extension of the line focus (x-direction) and across the focus (y-direction). However, any other measure of power drop-off could be used, such as the inverse e-squared value (1/e2).

Figure 10:
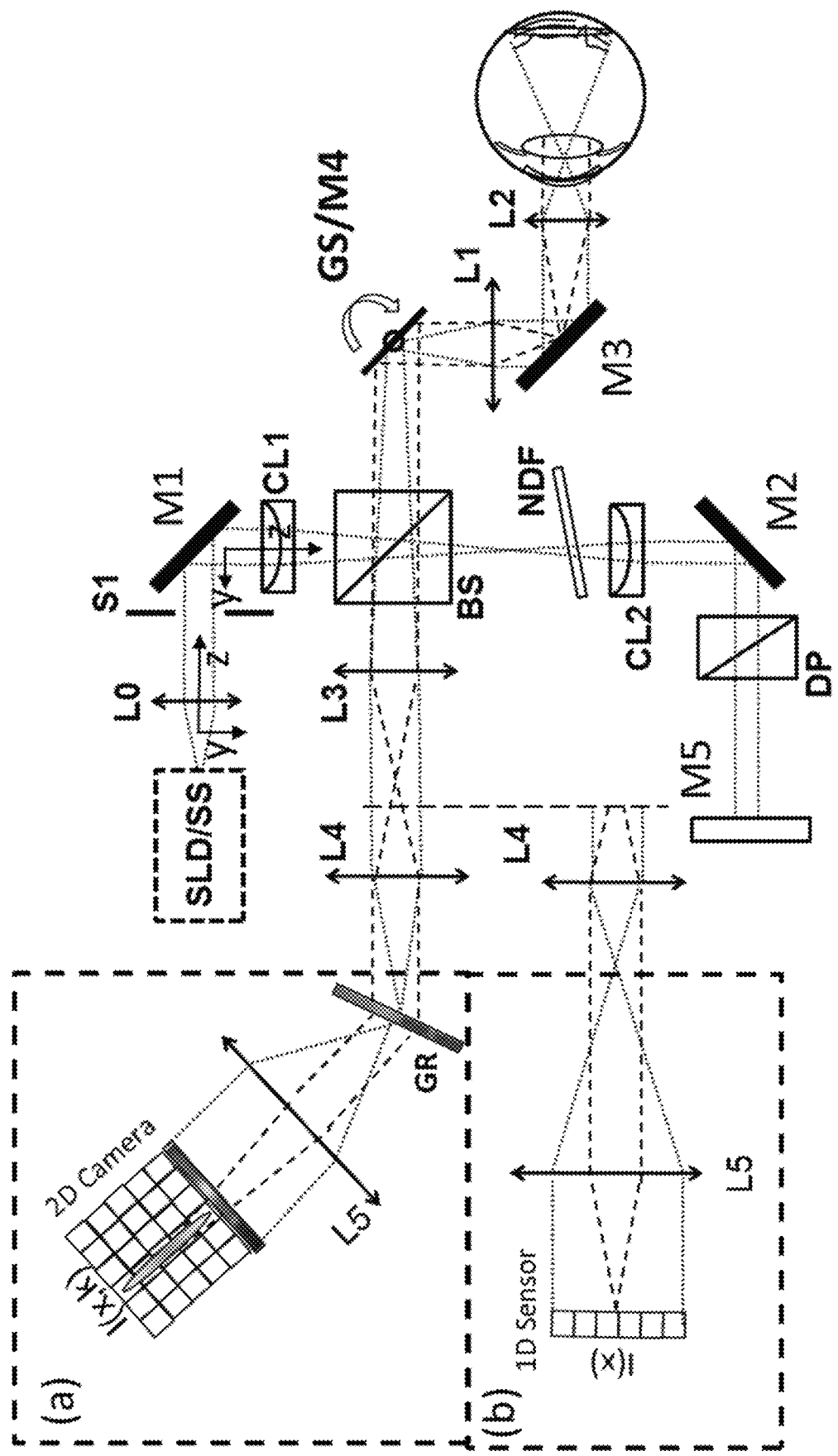
FIG. 10 is a schematic diagram of an example OCT system design using line-field illumination that incorporates a source module according to FIGS. 2 to 4, or FIGS. 5A & 5B, or FIG. 8 for coupling the source light into the system.

FIG. 10 is a schematic drawing of two variants of a line-field Fourier domain OCT system employing the proposed management of the elliptical beam in a source module according to the invention as described in relation to FIGS. 1 to 9. The illustrated axes yz (with axis x perpendicular to the paper) correspond to those in FIGS. 1 to 9 and apply to the light beam emitted from the source SLD/SS, so that these axes need to be correspondingly transformed by 90 degrees after mirror M1. With reference to FIGS. 1 to 9, collimating lens L0 corresponds to lenses 3 or 3a/3b and cylindrical lens CL1 corresponds to lens 6.

Two variant configurations (a, b) are shown for the detector.

Configuration (a) is a spectral domain system using a broad band source and a detector comprising a grating to separate the wavelengths spatially so that the separated spectra are projected onto a two-dimensional (2d), i.e. array, sensor. Configuration (b) is a swept source configuration, in which, for the detector, instead of using a grating only an achromatic lens is used, which focuses the light onto a one-dimensional (1d), i.e. line, sensor, in which case the spectra from the different wavelengths are acquired in a time series as the source is swept.

The parts shown in FIG. 10 are as follows:

| | |
|---|---|
| SLD | superluminescent diode (i.e. source) |
| SS | swept source |
| S1 | Slit |
| CL1 | cylindrical lens |
| GS | single-axis galvanometric scanner |
| BS | beam splitter |
| L0-L5 | achromatic lenses |
| NDF | neutral density filter |
| M1-M4 | Mirrors |
| DP | dispersion prism |
| GR | diffraction grating |

The source, superluminescent diode SLD for configuration (a), or swept source SS for configuration (b), outputs an elliptical beam which passes through slit S1, is reflected 90 degrees by a plane mirror M1 and is then focused by cylindrical lens CL1. A beam splitter BS is arranged to split the light into a first component and a second component. The first component traverses a sample arm by being projected onto a single-axis galvanometer scanner GS for a dynamic line-field OCT system (or onto a mirror M4—not shown, but arranged in the same place as scanner GS, for a static line-field OCT system). The light is reflected by approximately 90° from the galvo scanner GS (or exactly 90° from the mirror M4). The focal distance of CL1 is chosen to be on the galvanometer scanner GS (or mirror M4). The beam is collimated by lens L1, projected onto mirror M3 and once again focused using lens L2. A human eye is placed with its lens being at the focal position of lens L2 as illustrated. The light which is backscattered from the retina is directed back through the same path until beam splitter BS. At the beam splitter BS the backscattered component interferes with the second component returning from the reference arm. Meanwhile, in the reference arm, the source light after passing for the first time through the beam splitter BS passes through a neutral density filter NDF to adjust the power; after that it is recollimated by cylindrical lens CL2 and reflected by 90° using mirror M2. It further passes a dispersion prism DP to compensate for the dispersion in the sample arm. It is reflected by 180° with mirror M5. The reflected beam then goes back through the same path in the reference arm until it reaches the beam splitter BS, where it interferes with the backscattered component from the sample arm. From the beam splitter BS the combined components from the sample and reference arms are projected via lenses L3 and L4 into the detector sub-assembly. In configuration (a), the detector comprises a diffraction grating GR which spatially separates the wavelength components and projects them onto a 2d sensor via a collimating lens L5, this 2d setup being suitable in a spectral domain configuration using a broadband source such as the superluminescent diode SLD. It will be understood that the illustrated transmission diffraction grating GR could be replaced by a reflection diffraction grating. In configuration (b), the light from lens L4 is passed to a collimating lens L5 which projects the light onto a 1d line sensor, this 1d sensor setup being suitable if using a spectral domain arrangement or a (wavelength) swept source such as a swept source laser or a semiconductor optical amplifier (SOA). More details describing this setup can be found in [3,4], the full contents of which is incorporated herein by reference.

While a human eye is illustrated as a possible "sample" for investigation, the same apparatus design may be used for any desired sample. For example, one known further application of OCT is for measuring the topography of blind holes and/or through holes (so-called vias) in printed circuit boards (PCBs) or semiconductor wafers. Such an application using a spectral domain OCT system is described for example in CN103115580A [5]. This prior art document uses a 2D scanning galvanometer mirror to scan over the PCB. In our system implementation, a 1D scanning galvanometer mirror would be used, which would be quicker.

With reference to FIGS. 1 to 9, it will be understood that the source module includes the following components of FIG. 10: SLD/SS, L0, S1, M1 and CL1. If desired the source module may additionally accommodate further downstream components of the OCT system such as the beam splitter BS, or the beam splitter BS and GS/M4.

We have shown a highly specific OCT line-field configuration, by way of example only, but generally any line-field OCT system would profit from the proposed management of the elliptical beam according to the invention as described in relation to FIGS. 1 to 9.

Figure 11:
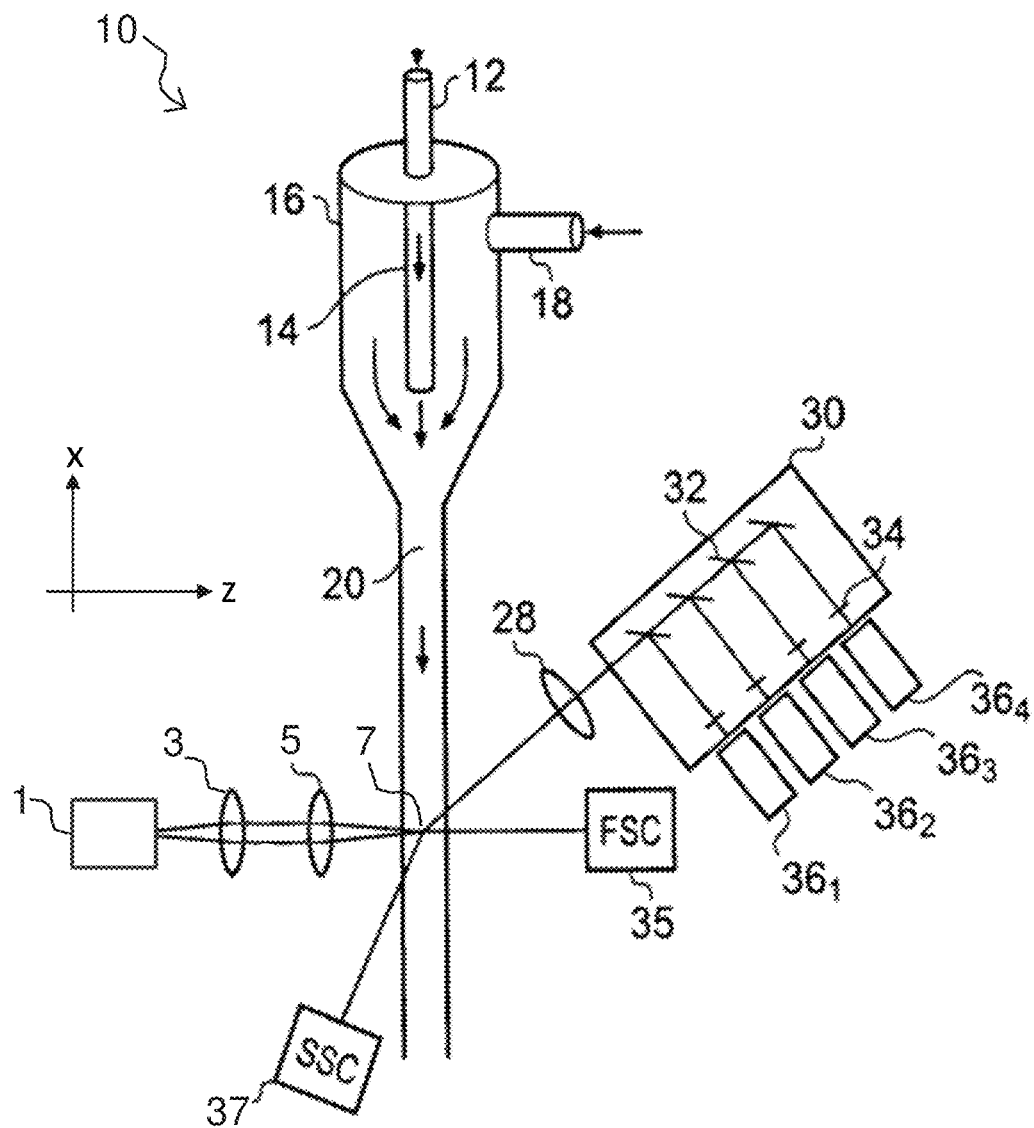
FIG. 11 is a schematic diagram of an example flow cytometer design using line-field illumination that incorporates a source module according to FIGS. 2 to 4, or FIGS. 5A & 5B, or FIG. 8 for coupling the source light into the flow cell region of the flow cytometer.

FIG. 11 is a schematic diagram of an example flow cytometer design using line-field illumination that incorporates a source module according to FIGS. 2 to 4, or FIGS. 5A & 5B, or FIG. 8 for coupling the source light into the flow cell region of the flow cytometer. Flow cytometers are widely used for analyzing properties of cells that are suspended in a liquid. The liquid is passed through a conduit so that the cells flow past a fluorescence-based sensing device one at a time. The cells can thus be counted and classified according to their spectroscopic properties which can then optionally be used to further direct the flow or for other purposes. For example, the cells can be sorted downstream of the detection device according to their fluorescence properties. This is usually referred to as fluorescence activated cell sorting (FACS). The flow cytometer has a flow cell 10 which receives a sample inlet tube 12. The sample inlet tube 12 is connected to an inner capillary tube 14 of the flow cell 10 which is radially enclosed prior to its termination by a sheath 16 which has a sheath inlet 18 connected to a sheath fluid inlet tube (not shown). As considered in the flow direction, the sheath 16 reduces in its cross-sectional diameter and the inner capillary tube 14 terminates leaving the sample fluid and sheath fluid flowing together along a capillary tube 20. After this termination, the sample flows radially confined to the central region of the flow by virtue of laminar flow at the interface between the sample fluid and the sheath fluid. The aim of this sheath arrangement is to allow good optical access to the sample in a flow tube that is sufficiently large in diameter to avoid blockages. The various optical components for excitation and collection are arranged about a measurement region of the capillary tube 20. In particular, the flow cytometer has a source module according to FIGS. 2 to 4, or FIGS. 5A & 5B, or FIG. 8 comprising a source 1 emitting a divergent output beam that is collimated by collimation optics 3 into a collimated beam and an optical sub-system 5 that focuses the elliptical collimated beam 4 to a line 7 in the focal plane f with the line focus extending in the flow direction, which is the x-direction, to intersect with sample in the capillary tube 20, e.g. coincident with the central axis of the cylindrical capillary tube 20. The line focus is in the x-direction and has a narrow width in the y-direction (out of the paper in FIG. 11). Fluorescence from the sample excited by the source 22 is then collected through a collection lens 28 and spectral sorting arrangement 30, comprising mirrors 32 and filters 34, which divides the fluorescence into different wavelength bands. Each color component is directed to a suitable photomultiplier tube (PMT) 361, 362, 363, 364 as illustrated with the example of four PMTs. A forward scatter (FSC)

detector 35 and side scatter (SSC) detector 37 may also be provided and are schematically depicted.

Line-field imaging modalities are, in the context of the invention, understood as including methods that illuminate the sample with a line. Line-field imaging modalities may use parallel detection along an array of sensor elements that records the line-field light backscattered or reflected from or transmitted through an object. The line may also be scanned across the sample, or the sample be moved relative to the illumination. The imaging technique may further employ interferometric signal modulation by using a reference arm such as in line-field OCT or line-field holography.

Example applications of the proposed management of the elliptical beam according to the invention as described in relation to FIGS. 1 to 9 further include: line-field imaging and sensing techniques, where the beam is kept static; line-field imaging and sensing techniques, where the beam is scanned across an object; line-field illumination, where the beam is kept static; and line-field illumination, where the beam is scanned. Line-field projection devices are, in the context of the invention, understood as including methods that steer a line-shaped beam across an object.

Figure 12:
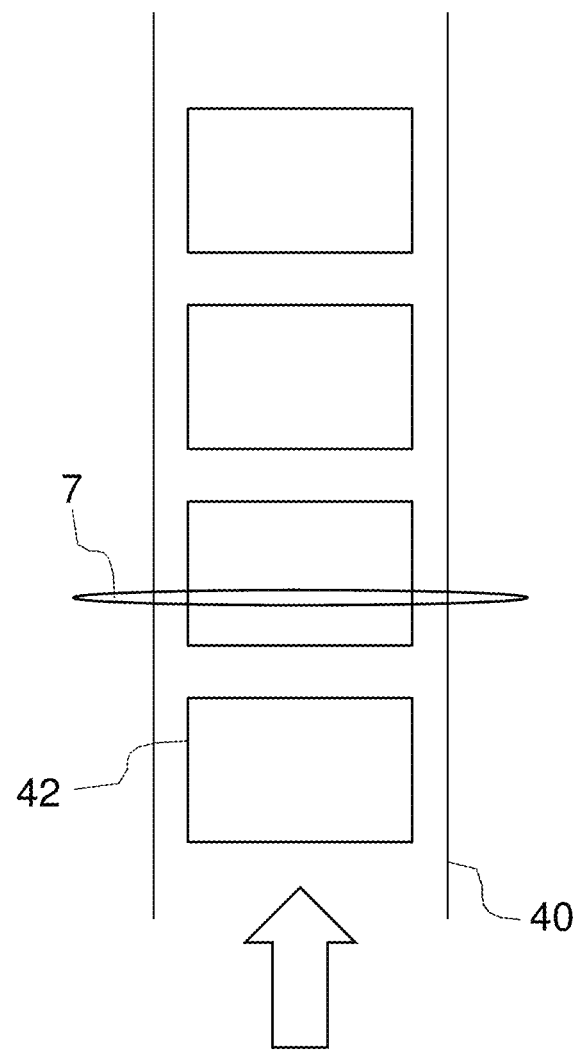
FIG. 12 is a schematic plan view of an OCT system embodying the invention being used to measure thickness uniformity of display panels.

FIG. 12 is a schematic plan view of an OCT system embodying the invention being used to measure properties of display panels, such as thickness uniformity and integrity and contamination of laminations or other bonding material, e.g. with foreign bodies, used to fuse panel layers together. The use of OCT for such an application is known from Cho et al [6]. A conveyer belt 40 conveys display panels 42 past a line focus 7 as output from the apparatus of FIG. 2 or FIG. 5A/5B. OCT is performed to measure the thickness of the panels, e.g. by measuring the vertical distance between upper and lower surfaces of a single piece of solid material, e.g. glass, or the vertical distance between surfaces that span an air gap as might be relevant for liquid crystal displays where the space formed by the gap is to be filled with liquid crystal. The line focus provides for more rapid scanning than a spot focus which would need to be scanned over the panel surface as in Cho et al ibid. Another specific example where a line focus is convenient is for inspection by OCT or other optical technique of a product for defects such as cracks or weld faults. If the product is elongate, like a railway rail, then the line focus can be arranged transverse to the rail as the line focus is moved along the rail.

Figure 13:
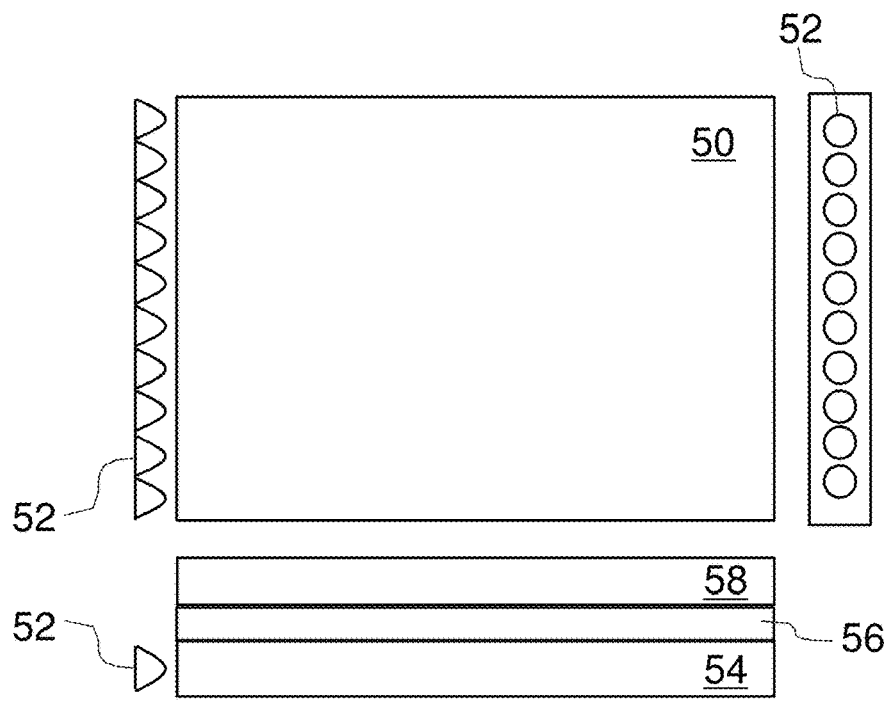
FIG. 13 shows a prior art edge-lit backlight unit for a display based on a strip of light emitting diodes (LEDs).

FIG. 13 shows in third-angle projection a prior art edge-lit backlight unit for a display 50 based on a strip of light emitting diodes (LEDs) 52. The LEDs emit into a light guide layer 54 which provides backlighting to the display panel 58, e.g. LCD or OLED, through a diffuser 56. The LEDs may be white, or a sequence of RGB emitters.

Figure 14:
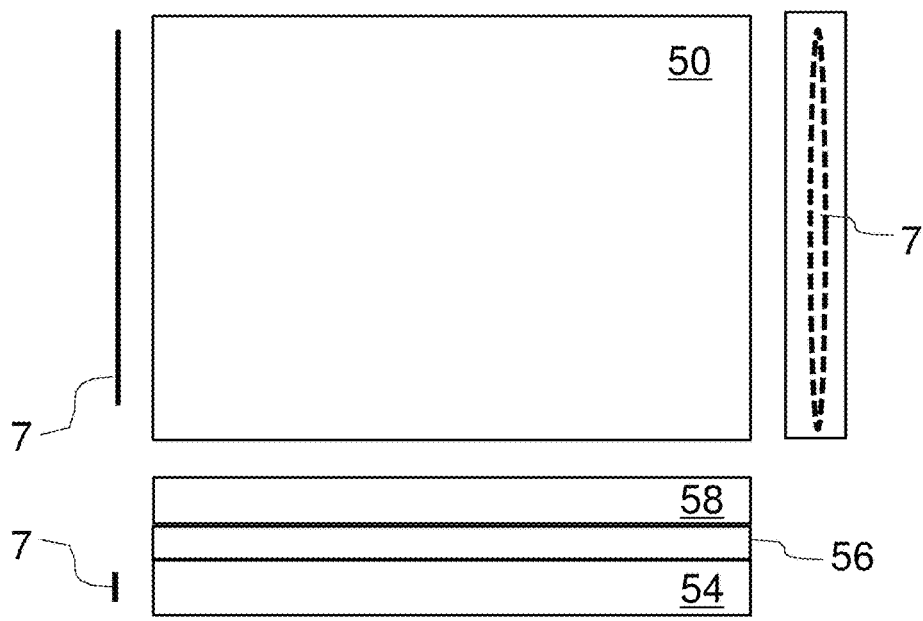
FIG. 14 shows an edge-lit backlight unit for a display according to an embodiment.

FIG. 14 shows an edge-lit backlight unit for a display according to an embodiment. By comparison with the prior art design, the LED strip is replaced with a line focus 7 as output from the source module of FIG. 2 or FIG. 5A/5B. The light guide layer 54 is arranged under the display panel 58. The source module is arranged with its line focus 7 aligned along an edge of the light guide layer 54. In this way, a much lower number of SLEDs may be used to replace a much larger number of LEDs.

Figure 15:
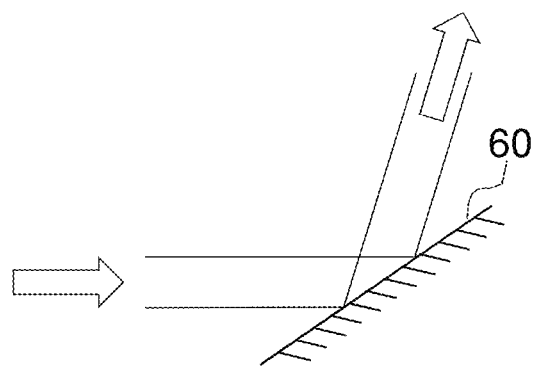
FIG. 15 is a schematic side view of a beam deflecting mirror arranged at an arbitrary angle to an incoming beam according to a further embodiment.

FIG. 15 is a schematic side view of a beam deflecting planar mirror 60 arranged at an arbitrary angle to an incoming beam according to a further embodiment. The effect of the mirror 60 is to transform the aspect ratio of the incoming beam in relation to the outgoing beam (unless the angle of incidence is 45 degrees). Since the outgoing beam will typically need to be delivered with a desired aspect ratio, e.g. 1:1, i.e. a circular-section beam, the arrangement of FIGS. 5A/5B can be used to tune the aspect ratio of the incoming beam to the value required to cause the outgoing beam to have a specified aspect ratio in cross-section. This can even be done dynamically by controlling the distance between lenses 3a and 3b, e.g. with a motor-driven linear translator, so that tilting of the mirror 60 at different angles can be compensated for during operation.

In further embodiments, the beam might also be spatially modulated, e.g. by using digital mirror devices, spatial light modulators or similar.

It will be clear to one skilled in the art that many improvements and modifications can be made to the foregoing exemplary embodiments as well as other embodiments without departing from the scope of the present disclosure.

REFERENCES

The full contents of the following references are incorporated herein by reference:
1. J. F. de Boer, R. Leitgeb, and M. Wojtkowski, "Twenty-five years of optical coherence tomography: the paradigm shift in sensitivity and speed provided by Fourier domain OCT [Invited]," Biomed. Opt. Express 8(7), 3248 (2017) [doi:10.1364/BOE.8.003248].
2. T. Bonin et al., "In vivo Fourier-domain full-field OCT of the human retina with 15 million A-lines/s," Opt. Lett. 35(20), 3432 (2010) [doi:10.1364/OL.35.003432].
3. D. J. Fechtig et al., "Line-field parallel swept source interferometric imaging at up to 1 MHz," Opt. Lett. 39(18), 5333 (2014) [doi:10.1364/OL.39.005333].
4. L. Ginner et al., "Noniterative digital aberration correction for cellular resolution retinal optical coherence tomography in vivo," Optica 4(8), 924 (2017) [doi:10.1364/OPTICA.4.000924].
5. CN103115580A
6. Cho, Park, Kim, Jung & Kim "Quantitative assessment of touch-screen panel by nondestructive inspection with three-dimensional real-time display optical coherence tomography" Optics and Lasers in Engineering, Elsevier 2014 [doi: 10.1016/j.optlaseng.2014.12.013]

What is claimed is:
1. An optical coherence tomography system, comprising:
a source module, the source module comprising:
a light source operable to emit a divergent, source output beam of circular or elliptical cross-section;
collimation optics arranged to convert the source output beam into a non-divergent, collimated beam of elliptical cross-section having a major axis and a minor axis; and
a line-focusing cylindrical lens having a plano axis and a power axis, which is arranged with its plano axis aligned with the major axis of the collimated beam and its power axis aligned with the minor axis of the collimated beam so as to form a line focus extending along the major axis of the collimated beam,
the system further comprising
a beam splitter arranged
to receive light output from the source module and
to direct one component into a first, sample arm to an optical test sample and another component to a second, reference arm, and
to recombine light received back from the first and second arms and direct the recombined light to a detector.

2. The system of claim 1, wherein the collimation optics comprises
   a first collimating cylindrical lens which collimates the source output beam in a first plane and
   a second collimating cylindrical lens which collimates the source output beam in a second plane orthogonal to the first plane,
   the first and second collimating cylindrical lenses being spaced apart by a distance which defines the ratio between the respective diameters of the major and minor axes of the collimated beam.

3. The system of claim 1, wherein the collimation optics comprises a spherical lens or an aspherical lens.

4. The system of claim 1, wherein the source output beam is of elliptical cross-section.

5. The system of claim 4, wherein the light source is an edge-emitting semiconductor source.

6. The system of claim 5, wherein the edge-emitting semiconductor source is one of a semiconductor laser, superluminescent diode, light-emitting diode, and semiconductor optical amplifier.

7. The system of claim 1, wherein the source output beam is of circular cross-section.

8. The system of claim 7, wherein the light source is one of a vertical cavity surface emitting laser and an optical fiber.

* * * * *